United States Patent [19]

Ferlic

[11] Patent Number: 4,472,828
[45] Date of Patent: Sep. 18, 1984

[54] X-RAY FILTER FOR CHEST X-RAYS

[75] Inventor: Daniel J. Ferlic, White Bear Lake, Minn.

[73] Assignee: Minnesota Mining and Manufacturing Company, St. Paul, Minn.

[21] Appl. No.: 401,368

[22] Filed: Jul. 23, 1982

[51] Int. Cl.³ .............................................. G21F 5/04
[52] U.S. Cl. ..................................... 378/147; 378/152
[58] Field of Search ......................... 378/147, 152, 153

[56] References Cited

U.S. PATENT DOCUMENTS

| 1,709,626 | 4/1929 | McGunnigle | 378/152 |
| 3,631,249 | 12/1971 | Friede et al. | 250/86 |
| 3,717,768 | 2/1973 | Edholm et al. | 250/86 |
| 3,950,651 | 4/1976 | Flocée | 378/147 |

FOREIGN PATENT DOCUMENTS

| 1402202 | 5/1965 | France | 378/147 |
| 187933 | 10/1966 | U.S.S.R. | 378/147 |
| 197773 | 4/1978 | U.S.S.R. | 378/153 |

OTHER PUBLICATIONS

Stanton, *Basic Medical Radiation Physics*, Meredith Corporation (New York: 1969) pp. 143-146.
Brochure published by Sheldon Enterprises, Inc., P.O. Box 996, Clearwater, Florida 33517.

*Primary Examiner*—Alfred E. Smith
*Assistant Examiner*—T. N. Grigsby
*Attorney, Agent, or Firm*—Donald M. Sell; James A. Smith; David L. Weinstein

[57] ABSTRACT

Filter for use in medical x-ray apparatus to permit higher intensity x-ray exposure in the heart and mediastinum area while maintaining a normal level of x-ray exposure in other areas of the body, particularly in the lung area. The filter comprises a sheet of radiation absorbing material having an opening therein, said opening corresponding to the spine and central portion of the heart. Accordingly, the upper portion of the filter exhibits a relatively narrow opening which becomes gradually wider toward the lower portion of the filter.

10 Claims, 6 Drawing Figures

X-RAY FILTER FOR CHEST X-RAYS

BACKGROUND OF THE INVENTION

This invention relates to a filter for x-ray examining devices.

A radiographic apparatus comprises, as well known in the art, as its fundamental components, a source of an ionizing and penetrative radiation, normally an x-ray tube, an object plane in which the object, or patient, to be radiographed is positioned, and an image plane on the opposite side of the object plane relative to the radiation source, in which image plane an image recording medium or device is disposed. The image recording medium may be a film sensitive to ionizing radiation, a fluorescent display screen or an electronic image amplifier.

When exposing chest x-rays, if the source of radiation is kept at a level that will provide a proper viewing density to the lungs, the level of radiation to provide acceptable exposure of parts of the body that are composed of dense tissue, e.g. the spine and the heart, will be insufficient.

It is an object of this invention to provide a means for maintaining an acceptable density level of x-ray exposure for the lungs while allowing a higher level of x-ray exposure in the heart and mediastinum areas of the body.

It is another object of this invention to provide a means for permitting a higher level of x-ray exposure in the heart and mediastinum areas of the body wherein such means can be easily adjusted for variations in (a) radiographic apparatus, (b) distance of radiation source from the patient, and (c) the physiology of specific patients.

SUMMARY OF THE INVENTION

This invention involves a filter for use in medical x-ray apparatus. The filter allows a relatively high intensity x-ray exposure in the heart and mediastinum area of the patient, while allowing a normal level of x-ray exposure in the other areas of the body, particularly in the area of the lungs.

The filter comprises a sheet of radiation absorbing material having a shaped opening of reduced radiation absorbing density in it in the area which would transmit radiation to the heart and mediastinum. Preferably the filter comprises a base plate forming a frame and open area therein, and two movable members made of radiation absorbing material, said movable members attached to said base plate by adjustable securing means such as nut and bolt assemblies. The bolts project through apertures in the movable members and further project through grooves in the base plate, said grooves defining the line along which said securing means move so that said movable members may be adjusted.

DETAILED DESCRIPTION

A conventional radiographic apparatus comprises (1) an object plane for an object, or patient, to be radiographed, (2) a source for a beam of penetrative radiation, i.e. x-rays, directed towards the object plane, (3) a radiation absorbing filter device positioned in the path of the radiation beam between the radiation source and the object plane. The x-rays traversing the object plane expose an x-ray film (directly or by means of an intensifying screen) which is then developed, yielding a permanent record of the x-ray image.

The filter device of the present invention comprises a material capable of absorbing x-ray radiation having areas of differential radiation absorption capability formed in a predetermined pattern or configuration. The filter can be formed of a single radiation absorbing sheet having the desired pattern cut into it. The required pattern in the sheet allows a higher level of x-ray exposure in the heart and mediastinum (spinal) areas of the body of a patient than in other areas of the body of the patient. It is preferable, however, to provide means for adjusting the filter for the purpose of adapting the filter for use on a variety of subjects or on a variety of radiographic apparatus.

A preferred filter construction comprises (a) a base plate forming a frame and an open area therein, (b) a plurality of movable members fastened to said base plate, said movable members forming a defined opening, said defined opening increasing in width from a relatively narrow area from the top to a wider area at the bottom of the base plate open area to provide a shaped pattern of greater exposure around the area of projected penetrating radiation corresponding to the human heart and around the area corresponding to the human spine and lesser exposure in the other areas of the body, and particularly in the area of the lungs. The pattern formed by the movable members is particularly desirable because a relatively high level of x-ray exposure (e.g., 250% of normal exposure levels) is required in the area of the spine and in the area of the central portion of the heart, both of which areas have high tissue density. It is not necessary that the opening defined by the movable members extend to include the outer portions of the heart. Because the outer portions of the heart have a lower density than does the central portion, the outer portions require a lower level of x-ray exposure for acceptable imaging. The movable members can be adjusted horizontally to provide for varying focal length of radiographic equipment, relative position of the filter with regard to the radiographic equipment and the patient, and the distance of the patient from the x-ray source. Vertical adjustments are provided by moving the entire radiographic apparatus in a vertical plane.

Figure 1:
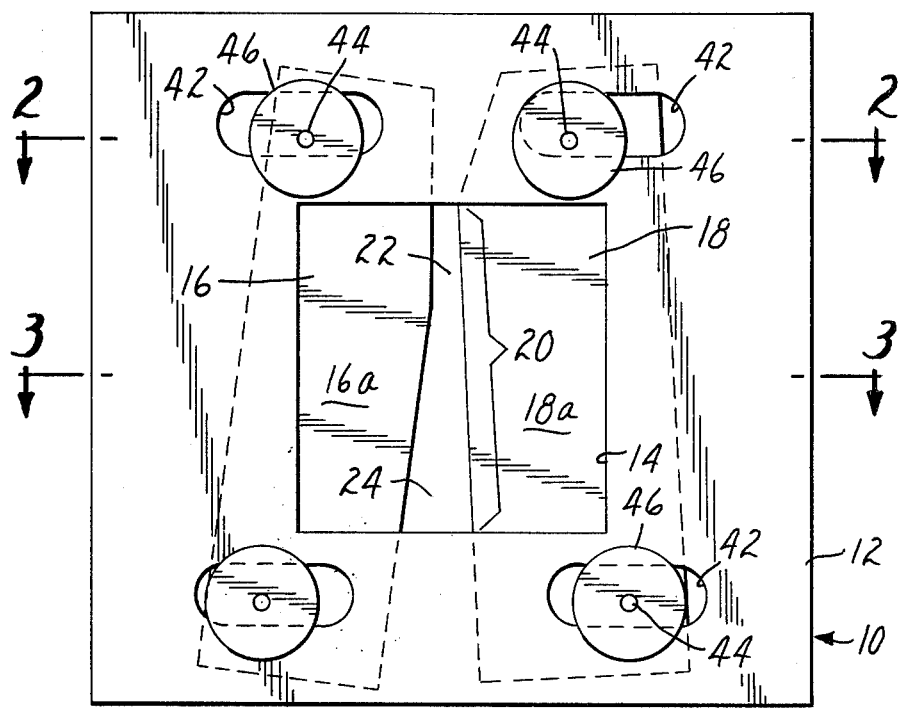
FIG. 1 is a plan view of the filter device.

FIG. 1 is a diagram of a preferred embodiment of the filter device. The filter device is useful with conventional x-ray apparatus.

The base plate 10 is a rectangular frame 12 having an open area 14 therein. Other configurations are acceptable, but a rectangular configuration is preferred for ease of assembly and operation. The base plate 10 may be formed from any material which is durable. The specific nature of the material of the base plate 10 is not critical. Suitable materials for the base plate 10 include metal, wood, and synthetic materials such as plastic. The preferred material is metal. Because of its high durability, steel is likely to be the metal of choice.

The movable members 16, 18 are made of material capable of absorbing x-ray radiation. The radiation absorbing material must absorb at least 50% of the incident radiation at a range of about 80 to about 180 Kvp (Kilovolt peak). The material may consist of a single material or a composite material. Suitable materials include aluminum, copper, tin, lead, and gold, as well as polymeric material filled with radiation absorbing materials. Aluminum, copper, and tin are most commonly used. Multi-layer filters which employ aluminum and copper cladding, or aluminum, copper, and tin are also commonly used. The preferred material is a multi-layer filter comprising a copper-clad aluminum. Thickness of the elements 16, 18 may conveniently range from 0.25 to 4.0 mm, although larger dimensions, depending upon radiation absorbing properties, are of course useful. The optimum thickness depends on (a) the material used in the filter, and (b) the purpose of the x-ray, e.g. diagnosis or therapy. Some representative thicknesses are as follows:

aluminum: 2-4 mm
copper: 1-2 mm
copper-clad aluminum: 0.25-1.0 mm copper; 1-2 mm aluminum Other suitable filter materials and filter thicknesses are disclosed in Stanton, Basic Medical Radiation Physics, Meredith Corporation (New York: 1969), pp. 143-146.

Figures 4, 5:
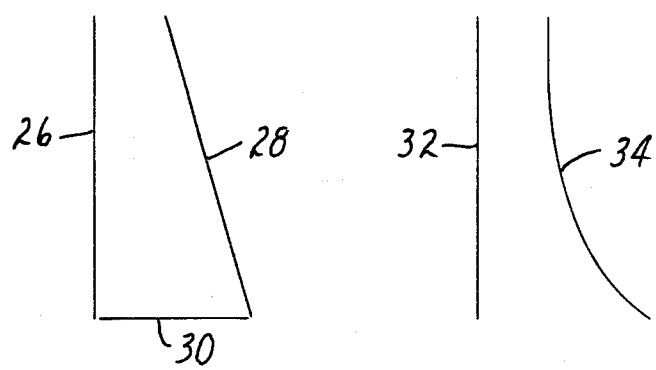
FIG. 4 is a schematic view of an alternative configuration for the pattern formed by the radiation absorbing material.
FIG. 5 is a schematic view of an alternative configuration for the pattern formed by the radiation absorbing material.
Figure 6:
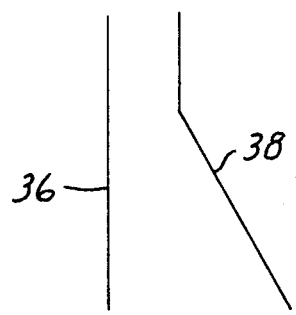
FIG. 6 is a schematic view of an alternative configuration for the pattern formed by the radiation absorbing material.

Regardless of whatever position the movable members 16, 18 are placed, the separation 20 between them is characterized by being relatively narrow in the area 22 corresponding in the object plane to the upper region of the spine and being relatively wide in the area 24 corresponding in the object plane to the portion of the heart having relatively high tissue density. The separation 20 preferably widens gradually from the upper portion of the base plate opening 14, i.e. the area corresponding to the spine, to the lower portion of the base plate opening 14, i.e. the area corresponding to the central portion of the heart. FIG. 4 shows representative configurations for the separation 20 between the movable members 16, 18. The minimum separation between the member 16 on the left and the member 18 on the right is in the area of the spine.

The character of the separation 20 in the filter through which x-rays will pass in an unobstructed fashion is extremely important in the practice of the present invention. As noted earlier, the top part 22 of the open area 20 is relatively narrow and then spreads out to a wider area 24 at the bottom of the opening 20. The separation 20 may be of any length as long as at least one portion of the separation 20 corresponds to the shape required for the practice of the present invention. For example, after the separation 20 has become wide enough at the bottom for complete exposure of the heart area, it may either sharply close (as shown in FIG. 1) or may taper into another narrow area or then close. The required configuration of the separation 20 to practice the present invention is at least one narrow portion at the top 22 which opens up to a wider portion at the bottom 24.

The size of the separation 20 at the top of the filter will vary depending upon the focal length of the radiographic equipment, the relative position of the filter with regard to the radiographic equipment and the patient, and the distance of the patient from the x-ray source. The purpose of the filter is to provide a shape of relatively intense x-ray exposure on the film which will correspond to the shape of the separation 20 in the filter. This exposure shape will provide high intensity exposure of the mediastinum area without correspondingly high exposure on the rest of the patient and without the formation of sharp lines of demarcation on the image from the filter. The area of direct, unobstructed exposure to radiation on the x-ray film or sensing device is intended to be at least ⅜ inch and no more than 1¾ inches in the upper portion of the image of the spine and no greater than 4½ inches at the bottom of the image over the area of the heart. Preferably, the exposure area at the top of the image on the film should be between ⅜ and 1¼ inch and the exposure at the bottom portion of the image should be between 2 and 4 inches. As indicated above, as long as a portion of the separation 20 in the filter provides the required type of imaging on the radiographic film, the shape of the opening in the filter above the narrow neck 22 and below the wide opening at the bottom 24 is not critical. Of course, it would be less desirable to have the separation 20 of the filter increase above the narrow neck and below the wide bottom area as this would increase the x-ray exposure of the patient, but this could be done if high intensity x-rays were contemporaneously desired of other parts of the patient. A mildly radiation absorbing layer could even be placed over the separation 20 or the entire filter, but without any known advantage.

The separation 20 may be in any form which will provide an open pattern which is narrow at the top and is wider toward the bottom. A simple triangular or truncated triangular form would be sufficient. This could be made with one side 26 of the separation 20 being relatively parallel to the spine of the patient and the second side 28 of the separation 20 being the other arm of the triangular form angled away from the parallel to form a wide base 30. This wide base area 30 in the filter would be positioned between the patient and the x-ray source so that the second side 28 extends towards the side of the patient on which the central portion of the patient's heart is located. Another alternative shape would be to have one side 32 of the separation 20 relatively parallel to the spine of the patient (e.g., relatively parallel to one side of the frame) and have the other side 34 of the separation 20 initially be relatively parallel to the first side 32 and then curve or bend away from the first side 32 to widen the area of exposure at the bottom of the separation 20 in the filter. The most prefered design is to have the first side 36 relatively parallel to the spine of the patient and have the second side 38 be relatively parallel to the first side or slightly angled away from the first side 36 at the top, narrow end 22 of the separation 20 and then increase the angle between the two sides 36,38 by having the second side 38 angled away from the first side at a point ¼ to ½ the distance from the top 22 to the bottom 24 of the separation 20. The angling away from the first side 36 would be to a divergent angle of between 10° and 40° away from the first side, preferably between 15° and 30°.

Figure 2:
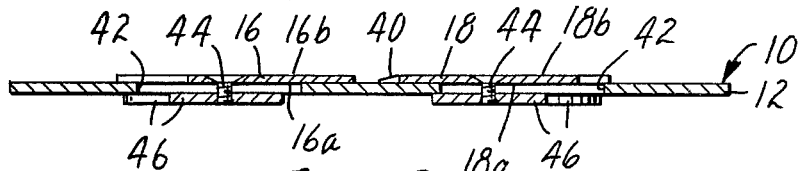
FIG. 2 is a sectional view taken along line 2—2 of FIG. 1.
Figure 3:
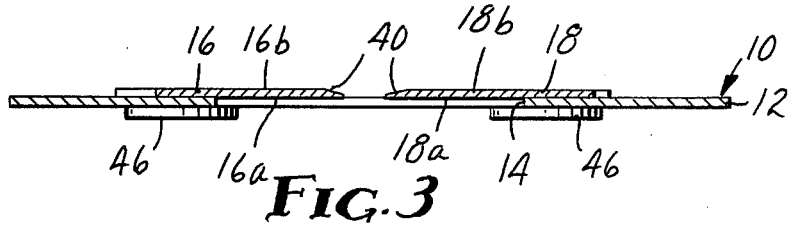
FIG. 3 is a sectional view taken along line 3—3 of FIG. 1.

Although it is possible to have the edges 40 of the radiation absorbing material 16, 18 which form the separation 20 in the filter to be cut at right angles to both faces 16a, 16b, 18a, 18b of the radiation absorbing material, it is highly preferred to have the edges 40 between the two faces 16a, 16b, 18a, 18b of the material cut at an angle so that the thinnest portion of the radiation absorbing material borders the opening on the pattern (a) cut into the radiative absorbing material, as in the case of a filter comprising a single sheet of radiation absorbing material, or (b) formed by the separation between the radiation absorbing members, as in the case of the embodiment shown in FIGS. 1, 2 and 3. Bevelling of the edge 40 of the radiation absorbing material would accomplish this. The greater the length of the incline formed by the bevelling, the greater the reduction in observable shadows that would be formed in the final image by the differential absorption of radiation between the opening and the unbevelled radiation absorbing material. When the bevelling is at least 20° away from a plane perpendicular to the face of the radiation absorbing material, shadow effects cannot readily be seen even by a trained radiologist. In view of the greater amount of radiation that is in fact absorbed by the radiation absorbing material, the inability to see shadows in the exposed image is quite surprising. It is preferred to have the bevelling at least 30° from that perpendicular plane and no more than 80°, which would cause the filter edge to become structurally weak. In order to prevent a razor-like edge from being formed on the interior of the opening, the edge may be filed or made slightly blunt in order to reduce the possibility of injuries to a worker in adjusting the filter opeining.

The separation 20 in the filter has been discussed with regard to the desired space on the imaged film. It is more difficult to measure the size of the opening itself, but the following dimensions would appear to generally apply. The top narrow area 22 should be no wider than 3/16 inch and no narrower than 3/64 inch. The base 24 should open to at least ⅜ inch and should be no wider than ⅓ inch. The height of the opening 20 should be at least 2 inches and less than 3½ inches. Again, it should be pointed out that the height of the opening 20 is not critical and that the opening may be substantially longer (and the dimensions at the extremes of the opening beyond the defined exposure area narrower and wider than heretofore defined), as long as there is at least one opening of these general dimensions and the described shape within the filter.

The movable members 16, 18 may be joined to the frame 12 base plate 10 in numerous ways. A particularly simple method of fastening the movable members 16, 18 to the base plate 10 involves providing grooves 42 in the frame 12 of the base plate 10 through which grooves 42 tightenable bolts 44 attached to said movable members 16, 18 may be inserted. The bolts 44 are preferably attached to the movable members by being inserted through apertures in the movable members.

These bolts include tightening nuts 46, the purpose of which is to secure the movable elements 16, 18 in a fixed position during the period of use of the x-ray apparatus. To alter the position of the movable members 16, 18, the tightening nuts 46 are loosened, the movable members 16, 18 are moved to the desired position along the line provided by the grooves 42, and the tightening nuts 38 are tightened.

The members 16, 18 are rendered movable in order to allow for adjustments in the specific location and dimensions of the separation 20 between the member 16, 18 depending upon the distance of exposure from the patient, the particular x-ray apparatus employed, and minor variations possible in the physiology of different patients.

In the preferred embodiment shown in FIG. 1 two movable members 16, 18 are shown. However, the same radiation absorbing capability as provided by one of the movable members 16 or 18 can be effected by employing a plurality of movable members, which, when property aligned, exhibit an appearance similar to member 16 or 18. For example, member 16 may be comprised of two component parts, each of which component part can be moved without moving the other component part. When the component parts of 16 would be properly aligned, the combination of component parts would appear identical to member 16.

Although the filter has been described with respect to the preferred embodiment as depicted in FIG. 1, it is not necessary that the filter comprise two or more elements, nor is it necessary that the filter have adjustable members. The filter can exhibit the required utility in a simple embodiment which comprises a single sheet of x-ray radiation absorbing material which has the specified pattern cut into it, so that it allows a higher level of x-ray exposure in the heart and mediastinum (spinal) areas of the body of a patient than in other areas of the body of the patient.

What is claimed is:

1. A filter device for use with a radiographic apparatus, said filter device comprising x-ray radiation absorbing material having a shaped opening therein which allows higher x-ray transmission therethrough in the heart and mediastinum areas of the body of a patient than in other areas of the body of the patient, said shaped opening being relatively narrow at the top and wider at the bottom, the edges of said radiation absorbing material disposed between the faces of said radiation absorbing material and delineating said shaped opening being bevelled.

2. The filter device of claim 1 wherein said radiation absorbing member is a sheet of radiation absorbing material adjustably secured to a frame.

3. Method of preparing a radiograph from radiographic apparatus comprising an object plane for an object to be radiographed, a source for a beam of penetrative radiation directed towards said object plane, a radiation absorbing filter device positioned in the path of said radiation beam between said source and said object plane, wherein said filter device is constructed according to claim 1, said method comprising directing a beam of penetrative radiation through the radiation absorbing filter device, and through the patient so that a greater amount of radiation passes through the mediastinum and central portion of the heart than through surrounding areas of the body, and exposing an x-ray film which can be developed to yield a permanent record of the x-ray image.

4. The method of claim 3 wherein said radiation absorbing member is a sheet of radiation absorbing material.

5. A filter device for use with a radiographic apparatus, said filter device comprising a base plate formed of a frame having an opening therein and x-ray radiation absorbing material comprising a plurality of x-ray radiation absorbing members attached to said base plate, said radiation absorbing members forming a shaped opening which allows higher x-ray transmission to the heart and mediastinum areas of the body of a patient than in other areas of the body of the patient, said shaped opening being relatively narrow at the top and wider at the bottom, the edges of said radiation absorbing members disposed between the faces of said radiation absorbing members and delineating said shaped opening being bevelled.

6. The filter device of claim 5 wherein the radiation absorbing members are movable along the frame of said base plate so that the shaped opening formed by the members can be adjusted.

7. The filter device of claim 5 wherein said radiation absorbing members are sheets of radiation absorbing material adjustably secured to said frame.

8. Method of preparing a radiograph from radiographic apparatus comprising an object plane for a patient to be radiographed, a source for a beam of penetrative radiation directed towards said object plane, a radiation absorbing filter device positioned in the path of said radiation beam between said source and said object plane wherein said filter device is constructed according to claim 5, said method comprising directing a beam of penetrative radiation through the radiation absorbing filter device, and through the patient to expose an x-ray film which can be developed to yield a permanent record of the x-ray image.

9. The method of claim 8 wherein the radiation absorbing members are movable along the frame of said base plate so that the shaped opening formed by the members can be adjusted.

10. The method of claim 8 wherein said radiation absorbing members are sheets of radiation absorbing material adjustably secured to said frame.

* * * * *

UNITED STATES PATENT AND TRADEMARK OFFICE
CERTIFICATE OF CORRECTION

PATENT NO. : 4,472,828

DATED : September 18, 1984

INVENTOR(S) : Daniel J. Ferlic

It is certified that error appears in the above-identified patent and that said Letters Patent is hereby corrected as shown below:

Col. 5, line 36, delete "1/3" and insert therefor --7/8--.

Claim 2, col. 6, line 37, delete "member" and insert therefor --material--.

Claim 4, col. 6, line 55, delete "member" and insert therefor --material--.

Signed and Sealed this

Nineteenth Day of March 1985

[SEAL]

*Attest:*

DONALD J. QUIGG

*Attesting Officer*   *Acting Commissioner of Patents and Trademarks*